US00RE38962E

(19) United States
(12) Reissued Patent
Rossi

(10) Patent Number: US RE38,962 E
(45) Date of Reissued Patent: Jan. 31, 2006

(54) DIPHENYL-TRIAZOLE DERIVATIVES AND THEIR USE AS ANTI-GESTATIVE IMMUNO-SUPPRESSANT AND ANTI-TUMORAL AGENTS

(75) Inventor: Carla Rossi, Milan (IT)

(73) Assignee: Geange Ltd., Dublin (IE)

(21) Appl. No.: 10/178,305

(22) PCT Filed: Jun. 4, 1998

(86) PCT No.: PCT/EP98/03496

§ 371 (c)(1),
(2), (4) Date: Jan. 28, 2000

(87) PCT Pub. No.: WO98/55463

PCT Pub. Date: Dec. 10, 1998

Related U.S. Patent Documents

Reissue of:
(64) Patent No.: 6,333,343
Issued: Dec. 25, 2001
Appl. No.: 09/445,218
Filed: Jan. 28, 2000

(30) Foreign Application Priority Data

Jun. 5, 1997 (IT) ..... MI97A1328

(51) Int. Cl.
*C07D 249/08* (2006.01)
*A61K 31/41* (2006.01)

(52) U.S. Cl. ..... 514/383; 514/399; 548/269.4; 548/343.5

(58) Field of Classification Search ..... 514/383, 514/399; 548/269.4, 343.5
See application file for complete search history.

(56) References Cited

U.S. PATENT DOCUMENTS 4,459,302 A * 7/1984 Omodei-Sale et al. ..... 514/383
4,535,090 A * 8/1985 Galliani et al. ..... 514/383
4,888,350 A * 12/1989 Omodei-Sale' et al. ..... 514/384

* cited by examiner

*Primary Examiner*—Joseph K. McKane
*Assistant Examiner*—Rebecca Anderson
(74) *Attorney, Agent, or Firm*—Nixon & Vanderhye P.C.

(57) ABSTRACT

Compounds of formula (I), wherein X and Y are independently carbon or nitrogen but not both simultaneously carbon, $R_1$ is a group (II) and $R_2$ is a group (III), $R_5$ being a carbonate, carbamate or phosphate residue, are useful as anti-gestative, immuno-suppressant and anti-tumor agents (I)

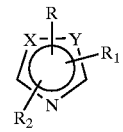

(II)

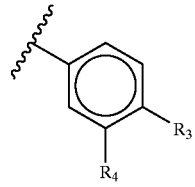

(III)

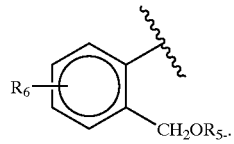

22 Claims, No Drawings

DIPHENYL-TRIAZOLE DERIVATIVES AND THEIR USE AS ANTI-GESTATIVE IMMUNO-SUPPRESSANT AND ANTI-TUMORAL AGENTS

Matter enclosed in heavy brackets [ ] appears in the original patent but forms no part of this reissue specification; matter printed in italics indicates the additions made by reissue.

This application is a 371 of PCT/EP98/03496 filed Jun. 4, 1998.

OBJECT OF THE PRESENT INVENTION

Objects of the present invention are nitrogen heterocyclic aromatic derivatives and their use as anti-gestative, immunosuppressant and anti-tumoral agents. Object of the present invention is also a procedure for the preparation of nitrogen heterocyclic aromatic derivatives.

Object of the present invention is again a pharmaceutical composition which contains, as active principle, at least one heterocyclic aromatic according to the present invention.

STATUS OF THE TECHNIQUE

Chemical classes of compounds endowed with anti-gestative activity are known, more specifically BE 866,728 reports a class of 3,5-diphenyl-1H-1,2,4 triazoles of the

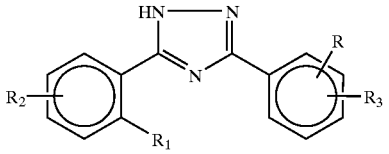

following general formula:

where $R_1$ is an alkyl group $C_1$–$C_4$.

EP11129 reports 1,2,4 triazoles derivatives of the following general structure:

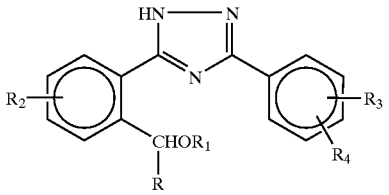

where R is hydrogen or methyl and $R_1$ is hydrogen or an alkyl group $C_1$–$C_4$, or $R_1$ and $R_2$ together form an additional bond between the carbon and oxygen atoms.

BE 879,732 reports a class of compounds showing the following general structure:

where, among the other possible substitutions, R is an

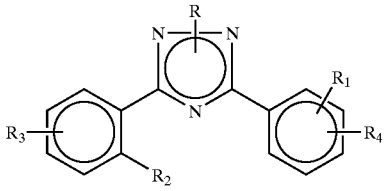

hydrogen or a $R_5$—CO group where $R_5$ is chosen among alkyl $C_1$–$C_4$, alkenyl $C_2$–$C_4$ and alkinyl $C_2$–$C_4$, whereas $R_2$ is a —$CH(R_7)OR_8$ where $R_7$ is an hydrogen or methyl and $R_8$ is like $R_5$—CO.

In the above mentioned disclosed documents, the pharmacological data show how these compounds display a high anti-gestative activity after repeated parenteral administrations (daily up to 5 consecutive days). The literature describes the compound 3-(2-ethyl-phenyl)-5-(3-methoxy-phenyl)-1H-1,2,4-triazole, also identified by the code DL 111-IT (Reviews on Drug Metabolism & Drug Interactions, Vol. IV, N. 2&3, 1982, A. Assandri, A: Omodei-Sale', G. Galliani).

The mentioned DL 111-IT, reported in BE 879,732, did show an interesting anti-gestative activity in all the investigated animal species including the mouse, the rat, the hamster, the dog and monkeys. DL 111-IT has been proposed as anti-gestative agent for human use.

These previously disclosed anti-gestative compounds, including the compound DL 111-IT, when tested according to a protocol which foresee a single dose parenteral treatment, displayed their activity at doses much higher than those required by multiple dose regimens. EP0080053 describes 3,5 diphenyl-1H-1,2,4 triazole derivatives that, as compared to the previously reported derivatives, have been structurally modified in order to obtain a high anti-gestative activity after a single-dose parenteral administration by subcutaneous and intramuscular route.

The compounds described in EP0080053 have the following general structure:

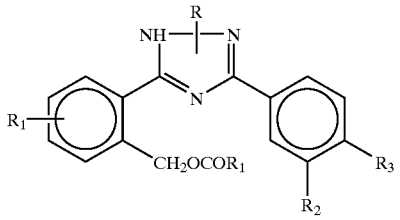

where, R is chosen between hydrogen and $R_5CO$—, where $R_5$ is a saturated or non-saturated aliphatic $C_1$–$C_{20}$ hydrocarbon chain, $R_1$, $R_2$ and $R_3$ are chosen among hydrogen and short-chain alkyl or alkoxyl, or $R_1$ and $R_2$ together form a methylendioxy group, $R_4$ is a saturated or non-saturated aliphatic $C_1$–$C_{20}$ hydrocarbon group.

The above mentioned derivatives, when given by single dose to rodents, displayed a high anti-gestative activity. This activity was however shown to be highly species-specific. Actually, while in rodents it was very high, in the higher mammal species, like the dog, the anti-gestative activity markedly decreased, due to a too slow hydrolysis rate of the administered products that undergo metabolism before the active principle become bioavailable.

OBJECTIVES OF THE INVENTION

Objective of the present invention is to make available nitrogen heterocyclic aromatic derivatives endowed with high anti-gestative activity when administered as single dose to different animal species including higher mammals and man.

Objective of the present invention is also to make available nitrogen heterocyclic aromatic derivatives endowed with high immuno-suppressant activity.

Again, objective of the present invention is to make available nitrogen heterocyclic aromatic derivatives endowed with non species-specific anti-gestative, immuno-suppressant and anti-tumour activity.

Again, objective of the present invention is to make available nitrogen heterocyclic aromatic derivatives endowed with a sustained duration of action, thus able to display the desired activity by a single-dose treatment (anti-gesative activity) or by multiple dose treatments with wide inter-administration time intervals (immuno-suppressant and anti-tumor acitvities).

Objective of the present invention is also to make available a pharmaceutical formulations, containing at least one nitrogen heterocyclic aromatic derivative as active principle, easy to be administered, well tolerated and able to allow a high therapeutic index.

DESCRIPTION OF THE INVENTION

These and other objectives with further advantages which are clarified in the description below, are obtained by the nitrogen heterocyclic aromatic dervatives having the following general formula:

(I)

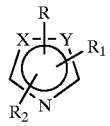

where:

when X=Y, X, Y=N;

when X=Y, X, Y=N, C, CH;

—R is chosen between hydrogen, —$COR_8$ where $R_8$ is a saturated or non-saturated $C_1$–$C_{10}$ aliphatic hydrocarbon, or R represents any other group able to form a bond with nitrogen atom;

—$R_1$ has the following genera formula:

(II)

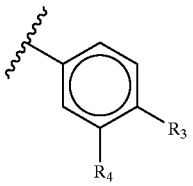

where $R_3$ is chosen among hydrogen, halogen, alkyl or alkoxyl $C_1$–$C_{10}$, $R_4$ is chosen among hydrogen, alkyl or alkoxyl $C_1$–$C_{10}$, or $R_3$ and $R_4$ together form a ethylendioxy group;

—$R_2$ has the following general structure:

(III)

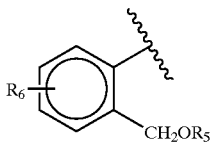

where $R_5$ is chosen among:

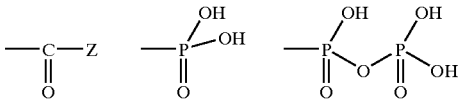

where Z=$OR_7$ with $R_7$ is chosen among a saturated or non-saturated, linear or branched $C_1$–$C_{20}$ aliphatic hydroacarbon, or is chosen according to the following formula:

(XII)

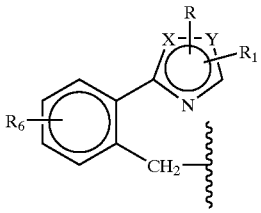

where R, $R_1$, X, and Y are defined as above and $R_6$ is chosen among hydrogen, halogen, alkyl or alkoxyl $C_1$–$C_{10}$, or Z is chosen equal to $NHR_8$ where $R_8$ is a linear or branched $C_1$–$C_{10}$ alkyl chain. Mentioned $R_1$ and $R_2$ are never located on two adjacent atoms of the heterocyclic aromatic ring.

Namely, the mentioned nitrogen heterocyclic aromatic derivative of formula (I) is a derivative of imidazole and 1H-1,2,4-triazole respectively:

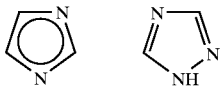

According to the present invention, the mentioned derivative of formula (I) is a triazole derivative having the following general formula:

(IV)

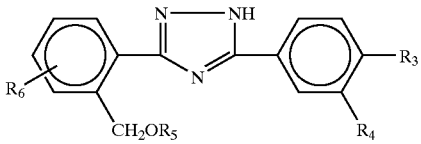

where X=Y=N, while the other substituents are defined as for the derivative of formula (I).

Of particular interest are those derivatives of formula (IV) where $R_6$ is hydrogen, $R_4$ is —$OCH_3$ or —$OCH_2$ $CH_3$, $R_3$ is hydrogen, $R_5$ is chosen equal to COZ where Z=$OR_7$ with $R_7$ as a saturated linear aliphatic $C_1$–$C_{12}$ hydrocarbon.

Always according to the present invention, of particular interest were those derivatives having the following formulas:

(V)

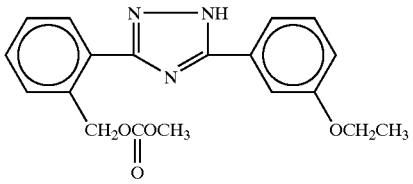

(VI)

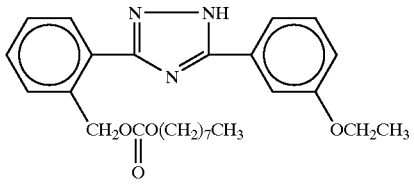

(VII)

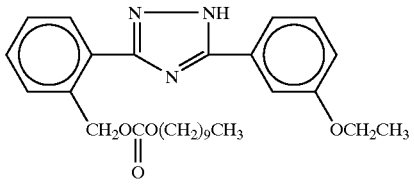

(VIII)

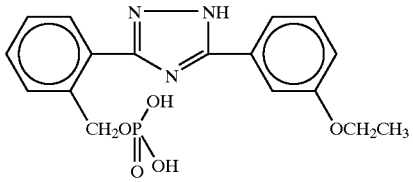

(XVI)

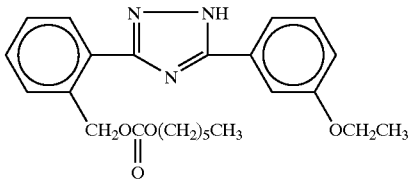

(XIII)

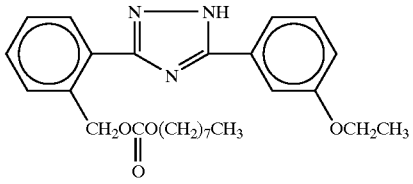

(XIV)

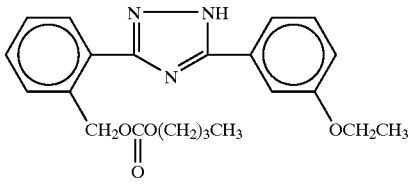

(XV)

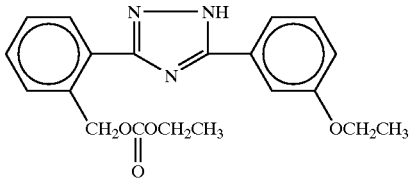

In addition according to the present invention, of particular interest were the two derivatives having the following formulas:

(XVII)

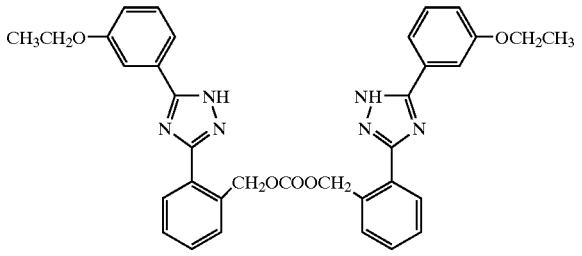

(XVIII)

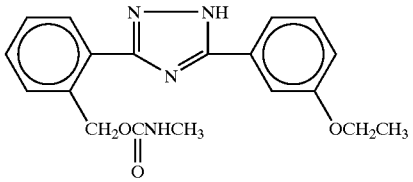

As reported in the literature, see Potts K. T, J: Chem. Soc. 3451, (1954) and Potts K. T., Chem. Rew. 61, 99 (1961), Kubota and Uda, Chem. Pharm. Bull. 23(5), 955 (1975), due to the high mobility of the hydrogen atoms of 1,2,4-triazoles, compounds of formula (I) of the present invention where X=Y=N, are to be regarded as a mixture of two tautomeric forms, i.e. those in which the hydrogen atom is located on one or the other of the two adjacent nitrogen atoms of the triazole ring. Depending on the nature of the substitutes at the 3 and 5 positions, a form may predominate on the other one. Consequently, both mentioned tautomeric forms must be considered as part of the present invention. It is known that tautomeric forms rapidly exchange in between and consequently behave as a dynamic equilibrium.

Anyway, throughout the whole description and claims relative to the present invention, 3,5 diphenyl-1H-1,2,4-triazoles according to the present invention, will be numbered as reported above for derivative (V).

The derivatives of the present invention are provided of anti-gestation, immuno-suppressive and anti-tumour activities. Particularly, the anti-gestative activity is displayed by a single dose regime and it does not requires a prolonged treatment. Furthermore, these derivatives show high therapeutic indexes, since a remarkable efficacy is achieved at doses much lower than the toxic ones able to induce undesirable adverse events. The compounds of the present invention of formula (I) when administered as a single parenteral injection displayed more than one pharmacological activity, namely:

(a) they have proven to be highly effective in terminating pregnancy in rodent and non-rodent animal species;

(b) they have proven to be highly effective in reducing both the humoural and cellular immunological response in animal models predictive for the pharmacological activity in humans (c) in addition, the compounds of the present invention while lacking of effectiveness in different tumour models, showed a specific marked activity on an model of human chorio-carcinoma transplanted in nude mice.

The different pharmacological activities displayed by the derivatives object of the present invention, are attributable to a common mechanism of action.

The reference model which explains this multiple pharmacological action is an atypical rapidly poliferating cell system, the placenta.

As repcorted Aitken, Beaconsfield and Ginsher in their comprehensive review origin and formation of the placenta this system, during its early stage of development, has strong similarties to tumor (1). Among these in particular, the placenta is tolerated by the maternal host due to an alteration of the immune responsiveness with no inflammatory response to blastocyst and/or throphoblast invasion.

Biochemical studies on placental tissue, during the early post-implantation period, demonstrated that the contragestational activity of 3,5 diaryl-1H-1,2,4-triazoles occurs through a selective action on the decidual and throphoblastic cells. Reasonably, this selective anti-proliferative action can also account for the activity of 3,5 diaryl-1H-1,2,4-triazoles against a gestational tumour like chorio-carcarcinoma. Finally, the immuno-suppressant response, which closely relates to the contra-gestational potency of 3,5 diaryl-1H-1, 2,4-triazoles, may either be the early or the late response of the primary biochemical alterations.

The derivatives object of the present invention are characterised by the presence of an easily hydrolysed bond through non species-specific enzymatic reactions occurring on $R_5$ group; this hydrolysis allows the release of the active principle that can display its in vivo action. The characteristic bond of $R_5$ group present in the derivatives object of the present invention, is different from the bonds described in the already disclosed derivatives, and it can be hydrolysed according to different mechanisms of reaction. Because of these properties, unlike the compounds already disclosed, the compounds objective of the present invention are also effective in higher mammal species, including humans. With the aim of evaluating whether inter-species difference could exist in the enzymatic reactions of the ester bond, compounds (XV), (XIV, VI) ad some known derivatives described in EP0080053 (compounds A, B and C) have been tested in vitro:

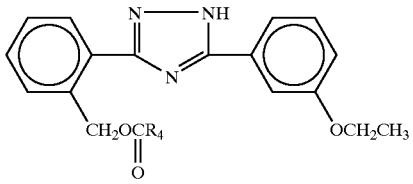

where when $R_4$ is chosen as —$C_3H_7$ the compound is named A;

where when $R_4$ is chosen as —$C_7H_{15}$ the compound is named B;

Where when $R_4$ is chosen as —$C_8H_{23}$ the compound is named C;

These compounds dissolved in an ethanol mother solution, when incubated in diluted (1:4 v/v, with saline, 0.9% NaCl) rat, dog and human serum at a $10^{-5}$ M concentration for 1 hour at 37° C. underwent enzymatic hydrolysis. The hydrolysis rates, expressed as n Moles/hour of the active principle formed, i.e. 3-(2-hydroxymethyl-phenyl)-5-(3#-ethoxyphenyl-1H-1,2,4 triazole, corresponding to the compound described in EP0080053, were measured. The values obtained, reported in Table 1, show how, in the higher species considered, i.e. the dog and man, the known products A, B and C undergo hydrolysis very slowly whereas compounds (XIV), (XV) and (VI), are rapidly metabolised both by rat, dog and human serum.

TABLE 1

HYDROLYSIS RATE OF SELECTED 3-(3-ETHOXYPHENYL)-5-(2-ACYL-CARBOXYMETHYL-PHENYL)-1H-1,2,4 TRIAZOLES, COMPOUNDS (XV), (XIV) and (VI) AND SELECTED 3-(3-METHOXYPHENYL)-5-(2-ACYLOXYMETHYL-PHENYL)-1H-1,2,4 TRIAZOLES, COMPOUNDS (A), (B) AND (C)

| | Rate of Hydrolysis (nmoles/hour) | | |
|---|---|---|---|
| COMPOUND | RAT | DOG | MAN |
| (XV) | ≧120 | ≧120 | ≧120 |
| A | ≧120 | 16 | 12 |
| (XIV) | ≧120 | ≧120 | ≧120 |
| B | ≧120 | 3 | 2 |
| (VI) | ≧120 | ≧120 | ≧120 |
| C | ≧120 | <0.5 | <0.5 |

Since the metabolic attack (de-alkylation) of these structures, occurring in position meta with respect to the substituent $R_1$ of structure (II), gives rise to inactive or poorly active metabolites, a too slow hydrolysis of compounds A, B and C will lead to a marked reduction of the activity of these molecules in the higher species. On the contrary, as already mentioned, derivatives of the present invention of formula (I), can be usefully used in higher mammal species including the dog and man. The compounds of the present invention actually represent a class of new non-hormonal, non-prostaglandin, like, post-coital, post-implantation anti-fertility agents particularly useful for terminating pregnancy in mammals following a single dose treatment at very low doses.

The pregnancy-terminating activity of the compounds of the present invention has been assessed by carrying out experiments in rats and dogs.

In particular, female Sprague Dawley rats weighing 200–230 g. were mated and the presence of sperm was detected, was considered day one of pregnancy.

Pregnancy was later confirmed at the time of autopsy by the presence of implantation sites in the uterus.

Test compounds dissolved in sesame oil containing 20% benzyl benzoate (or suspended if insoluble), were administered subcutaneously, in a single injection, on day 7 of gestation. The animals were then autopsied on day 16 of pregnancy and the uteri were examined for evidence of pregnancy (implantation sites, foetal resorption or live foetuses), haemorrhage, and evidence of abnormalities of the uterus, placenta or foetuses, for reference see G. Galliani et al. *Contraception,* 23, 163–180 (198).

The compounds were tested at different doses in order to study the dose-activity relationship and their activity, reported below in Table 2, has been expressed as $ED_{50}$ values.

These values identify the dose levels which terminate pregnancy (absence of live foetuses) in 50% of the treated animals. For comparison purposes, the $ED_{50}$ of some related triazoles previously disclosed (Belgian patents 866 , 728 and 879, 732 and European patent application publication No. 11,129), are reported.

In particular compound D (active principle), has the following structural formula:

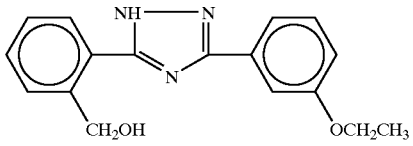

and it has been prepared as described in EP 11129, while compound E, prepared as described in BE 879732 and identified as DL111-IT, has the following formula:

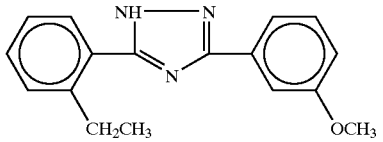

Table 2: Pregnancy Termination Activity in S.D. Rats After a Single Subcutaneous Injection at Day 7 of Gestation

TABLE 2

Pregnancy Termination Activity in S.D. Rats After a Single Subcutaneous Injection at Day 7 of Gestation

| Compound | $ED_{50}$ mg/kg | $ED_{50}$ μmoles/kg |
|---|---|---|
| (XV) | 15 | 27.2 |
| (XIV) | 8 | 20.3 |
| (XVI) | 5 | 11.8 |
| (VI) | 2 | 4.4 |
| D* | 16 | 54.6 |
| E** | 35 | 125.4 |

*5-(2-Hydroxymethylphenyl)-3-(3-ethoxy-phenyl)-1H-1,2,4-triazole described in the European patent application Publication No. 11, 129
**5-(2-Ethylphenyl)-3-(3-methoxyphenyl)-1H-1,2,4-triazole, DL 111-IT, described in example 24 of Belgian patent 879m732

The results obtained show how the compounds of formula (I) object or the present invention administered by a single parenteral injection are much more effective of the two compounds previously disclosed taken as reference.

Acute toxicity studies did show as the lethal doses of compounds (VI), $LD_{50}$>500 mg/kg, are of three order of magnitude higher than those anti-gestative.

In another experiment carried out in Beagle bitches (0.9–4.5 y, 7–12.5 kg), compound (VI), i.e. 3-(2-decanoyl-oxymethylphenyl)-5-(3-ethoxy phenyl)-1H -1,2,4-triazole, when administered as a single intramuscular dose between the day of mating and the 25th day of gestation was found to be highly effective and very well tolerated.

The compound was given intramuscularly in one depot site of the thigh muscle of the right hind leg dissolved in sesame oil at the dose of 5 mg/kg (11.1 μmoles/kg , 40 mg/mL, 0.2 mL/kg). The anti-gestative effectiveness was ascertained by exploratory laparatomy examining uterine horns where the presence of live or dead foetuses was deduced from the dimension and appearance of each uterine swelling, for methodological reference see G. Galliani et al., *J. Small Animal Practice,* 25, 211–222 (1984).

Table 3: Contragestational Effect of Compound (VI), Given as Single I.M. Doses Between the Day of Mating and the $14^{th}$ Day of Gestation.

TABLE 3

Contragestational Effect of Compound (VI), Given as Single I.M. Doses Between the Day of Mating and the $14^{th}$ Day of Gestation.

| Administration (days of gestation) | Dose (μmoles/kg) | No. of bitches | Pregnancy arrest (%) |
|---|---|---|---|
| 15 | 5 (11.1) | 5 | 80 |
| 20 | 5 (11.1) | 5 | 100 |
| 25 | 5 (11.1) | 5 | 100 |

The compounds of the present invention displayed significant immuno-suppressive activity on both humoral and cellular immunity when administered during the inductive phase of the immuno response, i.e. soon after antigen challenge. In experimental models of auto-immunity and skin transplantation they were able to reduce auto-antibody production as well as to prolong the skin graft survival.

The immuno-suppressant activity of the compounds of the present invention was assessed by carrying out experiments in mice.

In detail, the *Antibody Response to Sheep Red Blood Cells* (SRBC) and to Lipo-polysaccharide (LPS), was studied in B6D2F1 mice injected intravenously $10^8$ SRBC (day 0). Direct (IgM) and indirect (IgG) plaque forming cells (PFC) were evaluated in the spleen 4 and 10 days later, Jerne et al. *Science* 140, 405 (1963) and Dresser and Wortis, *Nature,* 208, 859(1965).

Indirect PCF were developed with rabbit anti-serum to mouse gamma globulin. B6D2F1 mice were immunised with 20 μg LPS intra-peritoneally. Four days later, PCF were determined in the spleen by SRBC coated with LPS, Moller, *Nature,* 207, 1166(1965).

TABLE 4

IgM ANTIBODY RESPONSE TO SRBC AND LPS AFTER SINGLE TREATMENT WITH COMPOUND (VI) COMPARED TO THAT OBTAINED AFTER MULTIPLE TREATMENT WITH THE REFERENCE COMPOUND E (see Mistrello et al., 1985)

| COMPOUND | ANTIGEN | DAY OF DOSING | DOSE (μmoles/Kg/day) | PCF/spleen. $10^{-3}$ (mean = S.D.) |
|---|---|---|---|---|
| (VI) | SRBC | 0 | vehicle | 124 + 18 |
| | SRBC | 0 | 8.60 | 12 + 3* |
| | LPS | 0 | vehicle | 10 + 2 |
| | LPS | 0 | 8.60 | 3 + 1* |
| | SRBC | 0, 1, 2, 3 | vehicle | 115 + 20 |
| | SRBC | 0, 1, 2, 3 | 17.92 | 7 = 2* |
| | LPS | 0, 1, 2, 3 | vehicle | 11 = 2 |
| | LPS | 0, 1, 2, 3 | 17.92 | 4 = 1* |

$p < 0.01$

TABLE 5

IgG ANTIBODY RESPONSE TO SRBC AFTER SINGLE TREATMENT WITH COMPOUND OF (VI) COMPARED TO THAT OBTAINED AFTER MULTIPLE TREATMENT WITH THE REFERENCE COMPOUND E (see Mistrello et al., 1985)

| COMPOUND | DAY OF DOSING | DOSE (μmoles/Kg/day) | PFC/SPLEEN.$10^{-3}$ (mean + S.D.) |
|---|---|---|---|
| (VI) | 0 | vehicle | 24 + 3 |
| | 0 | 2.15 | 3 + 3* |

TABLE 5-continued

IgG ANTIBODY RESPONSE TO SRBC AFTER SINGLE TREATMENT WITH COMPOUND OF (VI) COMPARED TO THAT OBTAINED AFTER MULTIPLE TREATMENT WITH THE REFERENCE COMPOUND E (see Mistrello et al., 1985)

| COMPOUND | DAY OF DOSING | DOSE (μmoles/Kg/day) | PFC/SPLEEN.$10^{-3}$ (mean + S.D.) |
|---|---|---|---|
| E | 0–3 | vehicle | 26 + 4 |
| | 0–3 | 3.58 | 4 + 3* |

Delayed Type hypersensitivity (DTH), was carried out in C57B1/6 mice administered subcutaneously $2\times10^8$ SRBC emulsified in complete Freund's adjuvant. Ten days later an eliciting dose of $10^8$ SRBC was inoculated into a footpad. The DTH reaction was recorded 24 hours later by measuring the footpad swelling (Kerckhaert et al, i Cell Immunology, 29, 232, (1977).

TABLE 6

EFFECT ON DTH AFTER SINGLE TREATMENT WITH COMPOUND OF COMPOUND (VI) COMPARED TO THAT OBTAINED AFTER MULTIPLE TREATMENT WITH THE REFERENCE COMPOUND E (see Mistrello et al., 1985)

| COMPOUND | DAY OF DOSING | DOSE (μmoles/Kg/day) | FOOTPAD SWELLING UNITS* (Mean + S.D.) |
|---|---|---|---|
| (VI) | 0 | vehicle | 11.4 + 3.7 |
| | 0 | 3.60 | 5.2 + 1.2** |
| E | 0, 1, 2, 3, 4, 5, 6, 7, 8 | vehicle | 10.1 + 3.3 |
| | 0, 1, 2, 3, 4, 5, 6, 7, 8 | 17.92 | 4.1 + 1.4** |

For the Skin Grafting, fitted pinch, grafts of skin from C3H (H-$2^k$) donor mice were transplanted onto C57B1/6 (H-$2^b$) recipient mice (Mistrello et al,. 1984) Bandages were removed 7 days later and graft were scored daily by microscopy. Rejection was recorded when no viable epidermis remained. The median survival time (MST) of the grafts, measured as days, was calculated according to Litchfield (1949).

TABLE 7

EFFECT ON SKIN GRAFT SURVIVAL TIME (MST) AFTER 1 WEEKLY TREATMENT WITH COMPOUND (VI) COMPARED TO THAT OBTAINED AFTER MULTIPLE TREATMENT WITH THE REFERENCE COMPOUND E(see Mistrello et al., 1985)

| COMPOUND | DAYS OF DOSING | Dose (μmols/Kg/day) | MST, days (mean ± S. D.) |
|---|---|---|---|
| (VI) | −1, 7 | vehicle | 10.7 + 0.4 |
| | −1, 7 | 17.20 | 15.1 + 0.6* |
| | −1, 1, 3, 5, 7 9, 11 | vehicle | 11.00 + 0.4 |
| | −1, 1, 3, 5, 7 9, 11 | 89.61 | 14.7 + 0.7* |

Finally, the compounds of the present invention are endowed with a high and specific anti-tumour activity as demonstrated on an in vivo test against human chario-carcinoma.

In particular compound of example 5 was highly effective in inhibiting the growth of a human chorio-carcinoma transplanted into nude mice. The potency of the tested compound was even higher than that displayed by methotrexate, the choice drug in the therapy of chorio-carcinoma.

Noteworthy, choriocarcinoma is a gestational tumor derived from trophoblastic cells, which, together with decidual cells, was suggested as the target site of the anti-proliferative action or 3,5 diaryl-s-1,2,4 triazoles (Galliani et al. 1986).

For their use in suppressing the immunological response, in terminating pregnancy, and in treating chorio-carcinoma, the compounds of the present invention are embodied into topical, transdermal and injectable dosage forms to be administered epicutaneously or parenterally, i.e. subcutaneously, intramuscularly or intravenously. Such composition are formulated using proper transdermal delivery systems (epicutaneous dosing), aqueous (intravenous dosing) or non-aqueous vehicles (epicutaneous, subcutaneous and intramuscular dosing).

As examples of such systems/vehicles, the following can be considered for epicutaneous, subcutaneous and intramuscular dosing: oils of vegetable origin or fatty esters such as sesame oil, corn oil, peanut oil, cotton seed oil, and ethyl oleate can suitably be employed.

Other oily vehicles may as well be used provided that they are safe in the volume administered and do not interfere with the therapeutic efficacy of the preparation. As known to the art skilled man, these preparations may also contain antimicrobial agents, to prevent growth of micro-organisms in the preparation, and antioxidants, essentially to prevent the development of rancidity of the oily vehicle.

These dosage forms in general contain from 1 to 10% (w/v) of at least one derivative or formula (I) object of the present invention, where the optimum dose/volume ratio depends on the selected dose and the species and size of the animal/subject to be administered As an example, the compounds of the present invention can be advantageously prepared starting from a derivative (IX) of the following chemical formula.

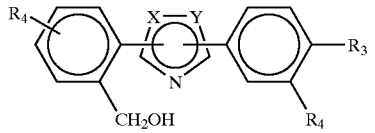

(IX)

More particularly, when substituents $R_1$ and $R_2$ are in position 3 and 5 respectively, the corresponding derivative (XI) has the following chemical formula:

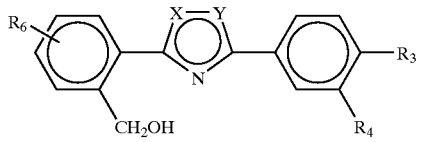

(XI)

The above mentioned derivative of Formula (XI), used as starting materials in the process of the present invention, is prepared according to different procedures already reported by the literature. In particular when X=Y=N, the corresponding derivative (XI a) can be advantageously prepared as described in EP11129. In this case the method.

This method consists in the rearrangement of hydrazones of substituted benzaldehydes with 4-hydrazino-1H-2,3-benzoxazines of formula (X)

(X)

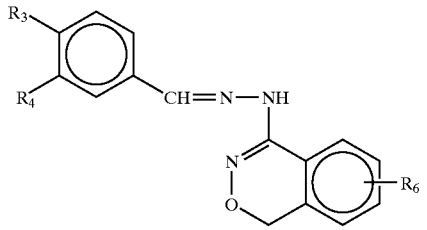

wherein $R_1$, $R_2$ and $R_3$ are as defined as for the derivatives of formula (I).

This rearrangement simply occurs by refluxing the hydrazone III in a high boiling inert organic solvent, such as for instance, xylene, N,N-dimethylformamide, and halogenated aromatic hydrocarbons, for about 30 minutes and then recovering the compound II by filtration.

Another suitable method for the preparation of the 2-hydroxymethyl-phenyl derivatives of formula (XI a), consists in the oxidation of the corresponding 2-methylphenyl triazoles, either directly to the alcohol (XI a) or to the corresponding carboxylic acid followed by a reduction of this latter to the alcohol (XI a).

In the former case, ceric ammonium nitrate or silver (II)oxide are the oxidising agents which may be suitably employed, while in the latter, the oxidative step is carried out with any of the several oxidisers known in the art to transform a methyl group on an aromatic ring to a carboxylic group, such as permanganate, nitric acid, and dichromate, and the reductive step in easily performed with a metal hydride.

Alternatively, the starting compounds of formula II can be prepared by following the process described in EP80053.

Referring to compounds of formula (I), object of the present invention, the procedure for their preparation starting from the corresponding derivative of formula (IX) varies depending whether the substituent R is hydrogen or a group $R_8$—CO wherein $R_8$ has the same meaning as above in relation to derivatives of formula (I).

When R is hydrogen, the derivative of formula (IX) is prepared according to different procedures already reported by the literature, in equimolar ratio with phosgene ($COCl_2$) and the resulting chloro-carbonate is left to react with a derivative Z where Z=$OR_7$ and $R_7$ is chosen among a saturated or non-saturated, linear or branched aliphatic hydrocarbon $C_1$–$C_{20}$, or is chosen according to the following formula:

(XII)

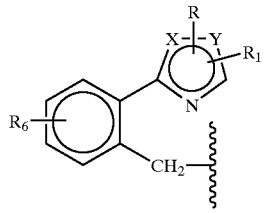

where R, $R_1$, X and Y are defined as above and $R_6$ is chosen among hydrogen, halogen, alkyl or alkoxyl $C_1$–$C_{10}$, or Z is chosen equal to NH—$R_8$ where $R_8$ is a linear or branched $C_1$–$C_{20}$ alkyl chain.

The derivative of formula (I) where R is chosen as hydrogen, can be successively separated from the possible by-products formed during the reaction with phosgene. Phosgene to use is commercially available already dissolved in appropriate solvents.

Following this procedure can be then prepared for example, derivatives (V), (VI) and (VII) of the present invention.

Alternatively, when have to be synthesised derivatives of formula (I) where $R_7$ is chosen as (XII), asymmetric carbonates, or when $R_7$ is chosen as saturated or unsaturated, linear or branched $C_1$–$C_{20}$ aliphatic hydrocarbon, derivative of formula (IX) can undergo reaction according to the following general scheme, in detail:

both for the intermediates preparation (alcoholate and imidazolide) and for the end carbonate product, an inert solvent is chosen, i.e. chloroform, dichloro-methane, tetrahydrofuran:

alcoholate recaratoon is carried out on the selected alcohol using as base NaH or matallic Na either in catalytic or stoichiometric amounts, temperature can be between 0° C. and 60° C. (optimal room temperature), while reaction time ranges between 30 min to 12 hours (optimal 1 hour);

the synthesis of the imidazolide of the second alcohol is carried out us na as reagent carbonyl-diimidazole with temperature between 0° C. and 60° C. (optimal, room temperature), while reaction time ranges between 30 min to 12 hours (optimal 1 hour);

the synthesis of the end carbonates products is carried out by mixing properly the solutions of the alcoholate and of the imidazolide for a time of 6 to 24 hours (optimal) 12 hours) at a temperature between 0° C. and 60° C. (optimal, room temperature).

Merely as an example, not limiting the present invention, a general method for the synthesis of derivatives of formula (I), where R and $R_3$ are chosen as hydrogens, $R_4$ is chosen as ethoxyl, $R_5$ is chosen as $COOR_7$ where $R_7$ is a linear or branched $C_1$–$C_{20}$ alkylic chain, is hereafter described:

EXAMPLE 1

A 50 mL solution of 3-(2-(hydroxymethyl)phenyl)-5-(3-ethoxyphenyl)-1H-1,2,4 triazole (3 g, 10 mmoles) in tetrahydrofuran, at room temperature, is added an 80% NaH suspension (310 mg, 10 mmoles) in tetrahydrofuran (50 mL). The reaction mixture is shacked at room temperature for 1 hour. The resulting solution is then added to a tetrahydrofuran solution containing the imidazolide of the selected alcohol obtained by reacting the alcoholic derivative (10 mmoles) with 1,1'-carbonyl-diimidazole (1.65 g, 10 mmoles) in tetrahydrofuran (20 mL) for 1 hour at room temperature. The mixture is stirred at room temperature for 12 hours, then solvent is take to dryness under vacuum and the residue re-dissolved in methylene chloride.

The organic phase is washed with water, dried by anhydrous $Na_2$ $SO_4$ and evaporated under vacuum. The obtained crude material is purified by column chromatography on silica gel (eluent hexane-ethylacetate, 8:2, v/v). After evaporation of the solvents, the solid pure product obtained is re-dissolved in hexane, filtered and dried under vacuum.

The compounds described below were prepared according to the procedure reported in Example 1.

EXAMPLE 2

Preparation of 3-(2-(ethoxy-carbonyloxymethyl) phenyl-5-(3-ethoxyphenyl)-1H-1,2,4-triazole (XV)

Yield 52%; melting point=124–126° C.

$^1$H-NMR: 7.98 (1H, t, J=4.1 Hz); 7.72–7.74 (6H, m); 7.06 (1H,d, J=6.9 Hz); 5.68 (2H, s); 4.16 (2H, q, J=7.0 Hz), 4.14 (2H, q, J=7.1 Hz); 1.40 (3H, t, J=7.0 Hz); 1.21 (3H, t, J=7.1 Hz).

$^{13}$C-NMR: 158.76, 154.21, 133.65, 129.83, 129.04, 128.77, 128.60 (2C), 118.16 (2C), 115.86, 112.04 (2C), 67.20, 63.33, 63.15, 14.36, 13.82.

EXAMPLE 3

Preparation of 3-(2-(butoxy-carbonyloxymethyl) phenyl-5-(3-ethoxyphenyl)-1H-1,2,4-triazole (XIV)

Yield 58%; melting point=119–121° C.

$^1$H-NMR: 8.00 (1H, t, J=4.8 Hz) ; 7.70–7.40 (6H, m) ; 7.03 (1H,d, J=7.2 Hz); 5.62 (2H, s) ; 4.12 (2H, q, J=7.0 Hz), 4.03 (2H, t, J=6.4 Hz); 1.49 (2H, m); 1.36 (3H, t, J=7.0 Hz); 1.23 (2H, m); 0.80 (3H, t, J=7.3 Hz).

$^{13}$C-NMR: 158.70, 154.29, 133.51, 129.89, 129.20 (2C), 128.63 (2C), 128.35 (2C), 118.15 (2C), 115.96, 111.98 (2C), 67.27, 67.17, 63.20, 18.03,14.26, 12.98.

EXAMPLE 4

Preparation of 3-(2-(hexyloxy-carbonyloxymethyl) phenyl-5-(3-ethoxyphenyl)-1H -1,2,4-triazole (XVI)

Yield 42%; melting point=90–92° C.

$^1$H-NMR: 8.07 (1H, m); 7.69–7.40 (6H, m); 7.06 (1H, d, J=7.3 Hz); 5.68 (2H, s); 4.15 (2H, q, J=7.0 Hz), 4.07 (2H, t, J=6.6 Hz); 1.56 (2H, m); 1.40 (3H, t, J=7.0 Hz); 1.23 (6H, m); 0.85 (3H, t, J=6.5 Hz).

$^{13}$C-NMR: 158.76, 154.29, 133.65, 129.79, 128.87 (2C), 128.59 (2C), 128.15 (2C), 113.15 (2C), 115.87, 112.03 (2C), 67.37, 67.29, 63.13, 30.49, 27.87, 24.52, 21.61, 14.36, 13.43.

EXAMPLE 5

Preparation of 3-(2-(octyloxy-carbonyloxymethyl) phenyl-5-(3-ethoxyphenyl)-1H-1,2,4-triazole (XVI)

Yield 49%; melting point=86–89° C.

$^1$H-NMR: 8.06 (1H, m); 7.72–7.40 (6H, m7); 7.05 (1H, d, J=7.1 Hz); 5.69 (2H, s); 4.15 (2H, q, J=7.0 Hz), 4.07 (2H, t, J=6.4 Hz); 1.56 (2H, m); 1.40 (3H, t, J=7.0 Hz); 1.23 (10H, m); 0.86 (3H, t, J=6.5 Hz).

$^{13}$C-NMR: 158.76, 154.28, 133.65, 129 77, 129.01, 128.84, 128.59 (2C), 128.59 (2C), 128.13 (2C), 118.16 (2C), 115.83, 112.03 (2C), 67.37, 67.30, 63.13, 30.83, 27.91, 24.89, 21.72,14.35, 13.53

In the following example 6, the synthesis of one derivative of formula (I), where the group $R_7$ is chosen of formula (XII), symmetric carbonates, is described

EXAMPLE 6

Preparation of Di-(2-(5-(3-ethoxyphenyl)-1H-1,2,4-triazol-3-yl) phenylmethyl) carbonate (XVII)

A 15 mL solution of 3-(2-(hydroxymethyl)phenyl)-5-(3-ethoxyphenyl)-1H-1,2,4 triazole (0.7 g, 2.4 mmoles) in tetrahydrofuran, at room temperature, is added a 80% NaH suspension (35 mg, 1.2 mmoles) in tetrahydrofuran (15 mL). The reaction mixture is shacked at room temperature for 1 hour. The resulting solution is then added 1,1'-carbonyl-diimidazole (192 mg, 1.2 mmoles) in tetrahydrofuran (20 mL) for 1 hour at room temperature. The mixture is stirred at room temperature for 12 hours. Solvent is taken to dryness under vacuum and the residue re-dissolved in methylene chloride. The organic phase is washed with water, dried by anhydrous $Na_2$ $SO_4$ and evaporated under vacuum. The obtained crude material is purified by column chromatography on silica gel (eluent hexane-ethylacetate, 7:3, v/v). After evaporation of the solvents, the solid pure product obtained is re-dissolved in hexane, filtered and dried under vacuum. 212 mg of the compound (XVII) are obtained.

Yield 36%; melting point=143–145° C.

$^1$H-NMR: 8.07 (2H, m), 7.69–7.38 (12H, m); 7.03 (2H,d, J=8.4 Hz); 5.72 (4H, s); 4.12 (4H, q, J=7.0 Hz), 1.37 (6H, t, J=7.0 Hz);.

$^{13}$C-NMR: 158.74, 154.21, 133.59, 129.81 (2C), 128.97 (2C), 128.02 (2C), 118.18 (2C), 115.88, 112.00 (2C), 67.41, 63.13, 14.33.

When R is chosen equal to —CO $R_8$, where $R_8$ is a saturated or a non saturated $C_1$–$C_{10}$ aliphatic hydrocarbon, the hydroxy group of derivative (IX), will be protected according to known methods. Protected derivative (IXb) will be also obtained and acylated according to known methods in order to introduce the —$COR_8$ group. Subsequently these acylated derivatives will be de-protected and allowed to react with phosgene as reported above. In the case of X=Y=N, th e acylation reaction could be carried out as described by EP80053.

When $R_5$ is chosen:

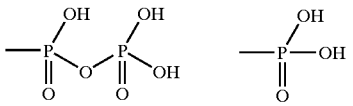

Derivatives of formula (I) are advantageously prepared starting from derivative s of formula (IX) (eventually submitted to a previous acylation reaction as already described) by reaction with phosphoric acid or equivalents according to known methods. For example, following this procedure derivative (VIII), object of the present invention, is prepared.

For derivatives of formula (I) , when X=Y=N and R=H, following the acylation procedure described above, both single compounds, where the substituent R is located on one of the two adjacent nitrogen atoms and mixtures of the two possible isomers can be obtained.

In this latter case, being established that each isomer retains the same anti-gestative immuno-suppressant and anti tumour activity, the mixture can be separated into the single components by chemico-physical known methods. For example, the way a mixture can be resolved into the single components is a fractionated crystallisation, which take advantage of the different solubility of each compound in various solvents at different temperatures. Suitable solvents that can be used for this method are chosen as an example, among hexane, ethyl-acetate, $C_1$–$C_4$ alkyl ethers, methylen chloride, light petroleum ether and mixtures thereof. A further illustrative example of a method useful for the separation of the isomers' mixture is based on column chromatography, performed on non-acid, buffered adsorbents, as silica-gel buffered to ph=7. Another example of a method useful for the separation of the isomer mixture is based on the use of preparative high pressure liquid chromatography (PHPLC), carried out on proper columns, for example filled with silica-gel esterified with octyl-silane or octyl-decylsilane. Other obvious procedures useful for resolving a mixture of isomers into the single components are intended to fall within the scopes of the invention.

What is claimed is:

1. A nitrogen heterocyclic aromatic derivative having the following general formula:

(I)

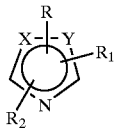

where X and Y are selected from N, C and CH, provided they are different from each other, or X and Y are both nitrogen;

R is hydrogen or —$COR_8$ where $R_8$ is a saturated or non-saturated $C_1$–$C_{10}$ alphatic hydrocarbon, $R_1$ has the following general formula:

(II)

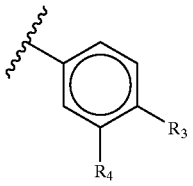

where $R_3$ is hydrogen, halogen, $C_1$–$C_{10}$ alkyl or $C_1$–$C_{10}$ alkoxyl, $R_4$ is hydrogen, $C_1$–$C_{10}$ alkyl or $C_1$–$C_{10}$ alkoxyl, or $R_3$ and $R_4$ together form a methylendioxy group, $R^2$ has the following general structure:

(III)

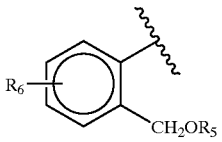

and $R_5$ is selected from:

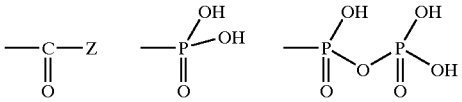

where Z=$OR_7$ where $R_7$ is a saturated or non-saturated, linear or branched $C_1$–$C_{10}$ aliphatic hydrocarbon, or $R_7$ has the following formula:

(XII)

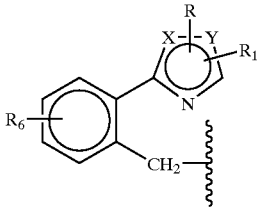

where R, $R_1$, X and Y are defined as above and $R_6$ is hydrogen, halogen, alkyl or alkoxyl $C_1$–$C_{10}$, or Z is $NHR_8$ where $R_8$ is a linear or branched $C_1$–$C_{20}$ alkyl chain, provided that when X=Y=N and R is H or —$CONHCH_2CH_3$, Z is not $NHR_8$ where $R_8$ is —$CH_2CH_3$, and provided that $R_1$ and $R_2$ are not located on two adjacent atoms of the heterocyclic aromatic ring, and further provided that when X=Y=N and $R_5$ is —COZ where Z=$OR_7$, $R_7$ is a saturated or non-saturated linear or branched $C_5$–$C_{20}$ aliphatic hydrocarbon.

2. The nitrogen heterocyclic aromatic derivative according to claim 1 wherein when $R_7$ is a saturated or non-saturated $C_1$–$C_{20}$ aliphatic hydrocarbon it is a linear or branched alkyl, alkenyl or alkinyl which may contain one or more double or triple bonds.

3. The nitrogen heterocyclic aromatic derivative according to claim 1 in which alkyl or alkoxyl is a linear or branched $C_1$–$C_{10}$ alkyl or alkoxyl group.

4. The nitrogen heterocyclic aromatic derivative according to the claim 1 wherein the ring structure of formula (I) is:

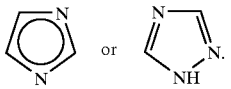

5. The nitrogen heterocyclic aromatic derivative according to claim 1 having the following general formula:

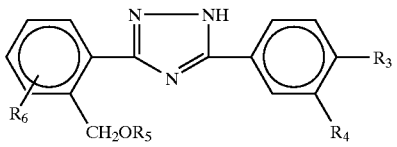

where $R_3$ is hydrogen, halogen, $C_1$–$C_{10}$ alkyl or $C_1$–$C_{10}$ alkoxyl, $R_4$ is hydrogen, $C_1$–$C_{10}$ alkyl or $C_1$–$C_{10}$ alkoxyl, or $R_3$ and $R_4$ together from a methylendioxy group, $R_5$ is one of:

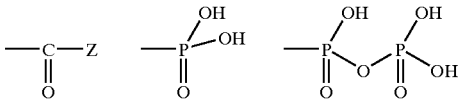

where Z=$OR_7$ where $R_7$ is a saturated or non-saturated, linear or branched $C_1$–$C_{20}$ aliphatic hydrocarbon, or is chosen from the following formula:

(XII)

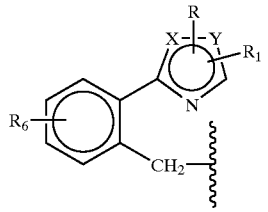

where R, $R_1$, X and Y are defined as above and $R_6$ is hydrogen, halogen, alkyl or alkoxyl $C_1$–$C_{10}$, or Z is $NHR_8$ where $R_8$ is a linear or branched $C_1$–$C_{20}$ alkyl chain, provided that when $R_5$ is —COZ where Z=$OR_7$, $R_7$ is a saturated or non-saturated, linear or branched $C_5$–$C_{10}$ aliphatic hydrocarbon.

6. The nitrogen heterocyclic aromatic derivative according to claim 5, wherein $R_6$=hydrogen, $R_4$=$OCH_3$ or $OCH_2CH_3$, $R_3$ is hydrogen, $R_5$ is COZ where Z=$OR_7$ where $R_7$ is a saturated linear alphatic $C_5$–$C_{12}$ hydrocarbon.

7. The nitrogen heterocyclic aromatic derivative according to claim 1 having the following structure;

(VI)

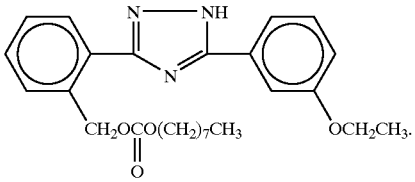

8. The nitrogen heterocyclic aromatic derivative according to claim 1 having the following structure:

(XVI)

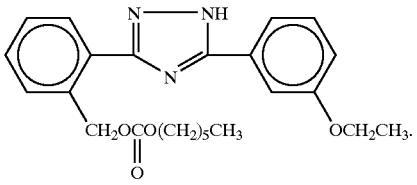

9. The nitrogen heterocyclic aromatic derivative according to claim 1 having the following structure:

(XIII)

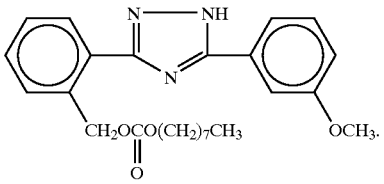

10. Nitrogen heterocyclic aromatic derivative having the following structure:

(XVII)

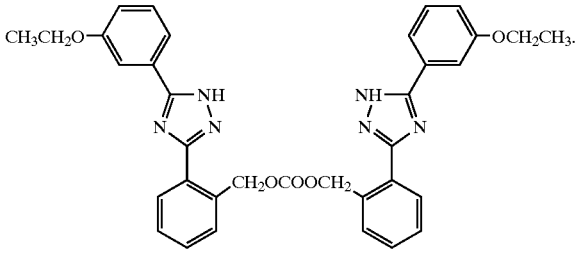

11. A pharmaceutical composition comprising a nitrogen heterocyclic aromatic derivative according to claim 1 together with a pharmaceutically acceptable diluent or carrier.

12. The pharmaceutical composition comprising a nitrogen heterocyclic aromatic derivative according to claim 10 in the form of a transdermal skin patch.

13. The pharmaceutical composition comprising a nitrogen heterocyclic aromatic derivative according to claim 10 for intravenous administration.

14. The pharmaceutical composition according to claim 11 wherein the diluent or carrier is a vegetable oil or an ester of fatty acid suitable for an epicutaneous, subcutaneous or intramuscular administration.

15. The pharmaceutical composition according to claim 14 wherein the diluent is sesame oil, corn oil, peanut oil, cotton seed oil or ethyl oleate.

16. The pharmaceutical composition according to claim 11 also including anti-microbic agent.

17. The pharmaceutical composition according to claim 11 also including an anti-oxidative agent.

18. The pharmaceutical composition according to claim 11 which contains from 1 to 10% (w/v) of the nitrogen heterocyclic aromatic derivative.

19. A method of terminating pregnancy in a mammal comprising administering an effective amount of a nitrogen heterocyclic aromatic derivative of claim 1.

20. A method of reducing the humoral and cellular immunological response of a mammal comprising administering an effective amount of a nitrogen heterocyclic aromatic derivative having the following general formula:

(I)

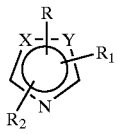

where X and Y are selected from N, C and CH, provided they are different from each other, or X and Y are both nitrogen;

R is hydrogen or —$COR_8$ where $R_8$ is a saturated or non-saturated $C_1$–$C_{10}$ aliphatic hydrocarbon, $R_1$ has the following general formula:

(II)

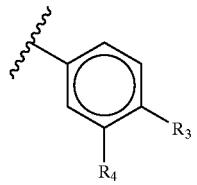

where $R_3$ is hydrogen, halogen, $C_1$–$C_{10}$ alkyl or $C_1$–$C_{10}$ alkoxyl, $R_4$ is hydrogen, $C_1$–$C_{10}$ alkyl or $C_1$–$C_{10}$ alkoxyl, or $R_3$ and $R_4$ together form a methylendioxy group;

$R_2$ has the following general structure:

(III)

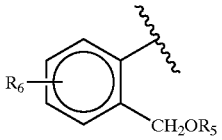

and $R_5$ is selected from:

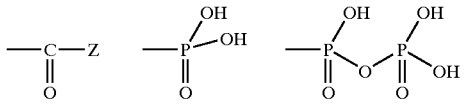

where Z=$OR_7$ where $R_7$ is a saturated or non-saturated, linear or branched $C_1$–$C_{10}$ aliphatic hydrocarbon, or $R_7$ has the following formula:

(XII)

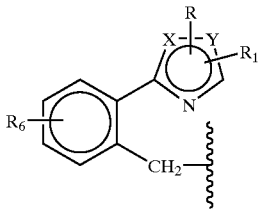

where R, $R_1$, X and Y are defined as above and $R_6$ is hydrogen, halogen, alkyl or alkoxyl $C_1$–$C_{10}$, or Z is $NHR_8$ where $R_8$ is a linear or branched $C_1$–$C_{20}$ alkyl chain, provided that when X=Y=N and R is H or —$CONHCH_2CH_3$, Z is not $NHR_8$ where $R_8$ is —$CH_2CH_3$, and provided that $R_1$ and $R_2$ are not located on two adjacent atoms of the heterocyclic aromatic ring, and further provided that when X=Y=N and $R_5$ is —COZ where Z=$OR_7$, $R_7$ is a saturated or non-saturated linear or branched $C_5$–$C_{20}$ aliphatic hydrocarbon.

21. A method of treating a tumor susceptible to therapy comprising administering an effective amount of a nitrogen heterocyclic aromatic derivative having the following general formula:

(I)

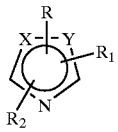

where X and Y are selected from N, C and CH, provided they are different from each other, or X and Y are both nitrogen;

R is hydrogen or —$COR_8$ where $R_8$ is a saturated or non-saturated $C_1$–$C_{10}$ aliphatic hydrocarbon, $R_1$ has the following general formula:

(II)

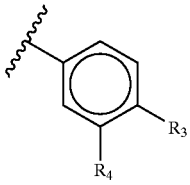

where $R_3$ is hydrogen, halogen, $C_1$–$C_{10}$ alkyl or $C_1$–$C_{10}$ alkoxyl, $R_4$ is hydrogen, $C_1$–$C_{10}$ alkyl or $C_1$–$C_{10}$ alkoxyl, or $R_3$ and $R_4$ together form a methylendioxy group;

$R_2$ has the following general structure:

(III)

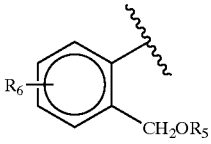

and $R_5$ is selected from:

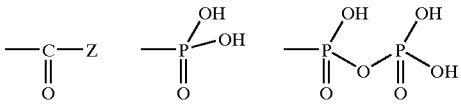

where Z=$OR_7$ where $R_7$ is a saturated or non-saturated, linear or branched $C_1$–$C_{10}$ aliphatic hydrocarbon, or $R_7$ has the following formula:

(XII)

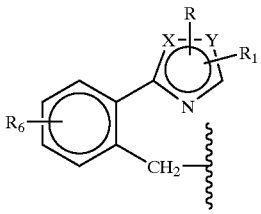

where R, $R_1$, X and Y are defined as above and $R_6$ is hydrogen, halogen, alkyl or alkoxyl $C_1$–$C_{10}$, or Z is $NHR_8$ where $R_8$ is a linear or branched $C_1$–$C_{20}$ alkyl chain, provided that when X=Y=N and R is H or —$CONHCH_2CH_3$, Z is not $NHR_8$ where $R_8$ is —$CH_2CH_3$, and provided that $R_1$ and $R_2$ are not located on two adjacent atoms of the heterocyclic aromatic ring, and further provided that when X=Y=N and $R_5$ is —COZ where Z=$OR_7$, $R_7$ is a saturated or non-saturated linear or branched $C_5$–$C_{20}$ aliphatic hydrocarbon.

22. A pharmaceutical composition comprising a nitrogen heterocyclic aromatic derivative according to claim 10 together with a pharmaceutically acceptable carrier or diluent.

* * * * *